(12) United States Patent
Cloud

(10) Patent No.: US 9,625,422 B2
(45) Date of Patent: Apr. 18, 2017

(54) 4C SLIP-SHOOTING METHOD AND DEVICE

(71) Applicant: CGG Services SA, Massy (FR)

(72) Inventor: Julien Cloud, Gentilly (FR)

(73) Assignee: CGG SERVICES SAS, Massy (FR)

( * ) Notice: Subject to any disclaimer, the term of this patent is extended or adjusted under 35 U.S.C. 154(b) by 924 days.

(21) Appl. No.: 13/962,168

(22) Filed: Aug. 8, 2013

(65) Prior Publication Data

US 2014/0041455 A1 Feb. 13, 2014

Related U.S. Application Data

(60) Provisional application No. 61/680,828, filed on Aug. 8, 2012.

(51) Int. Cl.
*G01N 29/04* (2006.01)
*G01V 1/38* (2006.01)

(52) U.S. Cl.
CPC ......... *G01N 29/045* (2013.01); *G01V 1/3861* (2013.01)

(58) Field of Classification Search
CPC ...... G01V 1/364; G01V 2210/46; G01V 1/32; G01V 2210/244
See application file for complete search history.

(56) References Cited

U.S. PATENT DOCUMENTS

| 8,797,828 B1* | 8/2014 | Lev | G01V 8/00 356/486 |
|---|---|---|---|
| 2012/0014212 A1* | 1/2012 | Eick | G01V 1/3808 367/23 |
| 2013/0121110 A1* | 5/2013 | Trad | G01V 1/364 367/63 |

* cited by examiner

*Primary Examiner* — Luke Ratcliffe
(74) *Attorney, Agent, or Firm* — Patent Portfolio Builders PLLC

(57) ABSTRACT

During a marine seismic survey, shots are fired at a time interval shorter than an S-wave listening time during which seismic receivers within a predetermined distance from the shot location detect reflected S-waves caused by an earlier shot. In portion of data acquired during the survey, information related to the S-wave reflections caused by the earlier shot is blended with information related to P-wave and S-wave reflections from a later shot.

20 Claims, 10 Drawing Sheets

Figure 3

| SPI | Single vessel single source | | | | Single vessel dual source | | | | Dual vessel single source | | | |
|---|---|---|---|---|---|---|---|---|---|---|---|---|
| | 12.5 | 25.0 | 37.5 | 50.0 | 12.5 | 25.0 | 37.5 | 50.0 | 12.5 | 25.0 | 37.5 | 50.0 |
| 5 | 4.9 | 8.0 | 8.0 | 8.0 | | 4.9 | 7.3 | 8.0 | | 4.9 | 7.3 | 8.0 |
| 6 | 4.0 | 8.0 | 8.0 | 8.0 | | 4.0 | 6.1 | 8.0 | | 4.0 | 6.1 | 8.0 |
| 7 | | 6.9 | 8.0 | 8.0 | | | 5.2 | 6.9 | | | 5.2 | 6.9 |
| 8 | | 6.1 | 8.0 | 8.0 | | | 4.6 | 6.1 | | | 4.6 | 6.1 |
| 9 | | 5.4 | 8.0 | 8.0 | | | 4.0 | 5.4 | | | 4.0 | 5.4 |
| 10 | | 4.9 | 7.3 | 8.0 | | | 3.6 | 4.9 | | | 3.6 | 4.9 |
| 11 | | 4.4 | 6.6 | 8.0 | | | | 4.4 | | | | 4.4 |
| 12 | | 4.0 | 6.1 | 8.0 | | | | 4.0 | | | | 4.0 |
| 13 | | 3.7 | 5.6 | 7.5 | | | | 3.7 | | | | 3.7 |
| 14 | | | 5.2 | 6.9 | | | | | | | | |

Recording time (seconds)

Recording time (seconds)

| SPI | Single vessel single source ||||  Single vessel dual source |||| Dual vessel single source ||||
|---|---|---|---|---|---|---|---|---|---|---|---|---|
|     | 12.5 | 25.0 | 37.5 | 50.0 | 12.5 | 25.0 | 37.5 | 50.0 | 12.5 | 25.0 | 37.5 | 50.0 |
| 5  | 7.3 | 8.0 | 8.0 | 8.0 | 3.6 |     | 8.0 | 8.0 | 3.6 | 7.3 | 8.0 | 8.0 |
| 6  | 6.1 | 8.0 | 8.0 | 8.0 |     | 6.1 | 8.0 | 8.0 |     | 6.1 | 8.0 | 8.0 |
| 7  | 5.2 | 8.0 | 8.0 | 8.0 |     | 5.2 | 7.8 | 8.0 |     | 5.2 | 7.8 | 8.0 |
| 8  | 4.6 | 8.0 | 8.0 | 8.0 |     | 4.6 | 6.8 | 8.0 |     | 4.6 | 6.8 | 8.0 |
| 9  | 4.0 | 8.0 | 8.0 | 8.0 |     | 4.0 | 6.1 | 8.0 |     | 4.0 | 6.1 | 8.0 |
| 10 | 3.6 | 7.3 | 8.0 | 8.0 |     | 3.6 | 5.5 | 7.3 |     | 3.6 | 5.5 | 7.3 |
| 11 |     | 6.6 | 8.0 | 8.0 |     |     | 5.0 | 6.6 |     |     | 5.0 | 6.6 |
| 12 |     | 6.1 | 8.0 | 8.0 |     |     | 4.6 | 6.1 |     |     | 4.6 | 6.1 |
| 13 |     | 5.6 | 8.0 | 8.0 |     |     | 4.2 | 5.6 |     |     | 4.2 | 5.6 |
| 14 |     | 5.2 | 7.8 | 8.0 |     |     | 3.9 | 5.2 |     |     | 3.9 | 5.2 |

Figure 12

Recording time (seconds)

| SPI | Single vessel single source |||| Single vessel dual source |||| Dual vessel single source ||||
|---|---|---|---|---|---|---|---|---|---|---|---|---|
|     | 12.5 | 25.0 | 37.5 | 50.0 | 12.5 | 25.0 | 37.5 | 50.0 | 12.5 | 25.0 | 37.5 | 50.0 |
| 5  | 50 | 0  | 0  | 0  | OK |    | 10 | 0  | OK |    | 10 | 0  |
| 6  | 50 | 0  | 0  | 0  |    | 50 | 32 | 0  |    | 50 | 32 | 0  |
| 7  | OK | 15 | 0  | 0  |    | OK | 50 | 15 |    | OK | 50 | 15 |
| 8  | OK | 32 | 0  | 0  |    | OK | 50 | 32 |    | OK | 50 | 32 |
| 9  | OK | 48 | 0  | 0  |    | OK | 50 | 48 |    | OK | 50 | 48 |
| 10 | OK | 50 | 10 | 0  |    | OK | 50 | 50 |    | OK | 50 | 50 |
| 11 |    | 50 | 21 | 0  |    |    | OK | 50 |    |    | OK | 50 |
| 12 |    | 50 | 32 | 0  |    |    | OK | 50 |    |    | OK | 50 |
| 13 |    | 50 | 43 | 7  |    |    | OK | 50 |    |    | OK | 50 |
| 14 |    | OK | 50 | 15 |    |    | OK | OK |    |    | OK | OK |

4C SLIP-SHOOTING METHOD AND DEVICE

CROSS REFERENCE TO RELATED APPLICATIONS

This application claims priority and benefit from U.S. Provisional Patent Application No. 61/680,828, filed Aug. 8, 2012, for "4C Slip-Shooting," the entire content of which is incorporated in its entirety herein by reference.

BACKGROUND

Technical Field

Embodiments of the subject matter disclosed herein generally relate to methods and devices used for marine seismic surveys, and, more particularly, to methods and devices used for firing marine seismic sources.

Discussion of the Background

Offshore drilling is an expensive process. Therefore, those undertaking offshore drilling use a profile (image) of the geophysical structure under the seafloor obtained by seismic surveys to avoid a dry well. However, due to the high cost of marine seismic surveys, there is continuous interest in decreasing their duration (i.e., increasing survey's productivity), while also increasing (or at least maintaining) data quality.

In a marine seismic survey, a vessel tows one or more sources that generate seismic waves. The seismic waves travel through the water and then penetrate the geophysical structure under the seafloor. The waves are reflected at interfaces between layers of the geophysical structure under the seafloor, with the layers differentiated by the different speeds at which the seismic waves propagate through them (i.e., a discontinuity occurs in the propagation speed as a function of depth at a layer interface). The reflected waves carrying information about layer characteristics and the location of layer interfaces are detected by seismic receivers.

Incident waves are P-waves (also known as pressure, longitudinal or primary waves). At a solid-solid interface (i.e., an interface between subsurface layers through which seismic waves propagate at different speeds), both P-waves and S-waves (also known as shear, transversal or secondary waves) may emerge as a consequence of incident wave's reflection and refraction. Reflected S- and P-waves carry complementary information. Generating an S-wave-based image in addition to the P-wave-based image gives access to an additional rock parameter (e.g., Poisson's ratio or simply the velocity ratio Vp/Vs), which enables better discrimination of the layers than P-wave-based imaging alone (e.g., allows better distinction of layers' porosity).

Since S-waves do not propagate through the water, seismic receivers are placed on the seafloor to detect both reflected P- and S-waves. Ocean bottom multi-component sensors (OBS 4C) are used in marine seismic surveys to detect both reflected P- and S-waves. For example, such an OBS 4C sensor may include a hydrophone and a three-component (3C) geophone, or a three-component (3D) accelerometer.

From the standpoint of generating incident seismic waves, marine surveys in which OBS 4C detect the seismic reflections may:

(1) use a single vessel towing a single source and achieving a productivity P;
(2) use a single vessel towing a dual source, including two sub-arrays triggered in flip-flop mode (i.e., alternating), achieving a productivity 2P; or
(3) use dual vessels, each towing a single source triggered in a radio-synchronized flip-flop mode, achieving a productivity (1+x)P, where x is the fraction of time the two vessels are online and shooting.

FIG. 1 schematically illustrates a marine survey system (bird's eye view) including a vessel 10 towing, along a trajectory line 15, a dual source 20 including sub-arrays 22 and 24. A controller C (which may be located on vessel 10) controls alternatively firing sub-arrays 22 and 24. A few shot locations 30, 32, 34 and 36 are illustrated in FIG. 1. A corresponding time line 50 is illustrated parallel to trajectory line 15. Along time line 50, time runs from the bottom to the upper part of the line. Rectangles 1, 2, 3 and 4 on time line 50 represent recording times during which a data acquisition system records data related to S- and P-wave reflections detected by seismic receivers following shots at locations 30, 32, 34 and 36, respectively. Conventionally, a shot is fired only after all the data pertaining to reflections from a previous shot have been recorded. Thus, rectangles 1, 2, 3 and 4 do not overlap.

FIG. 2 is a graph illustrating time distribution of data corresponding to two records following a pair of successive shots. The x-axis of the graph represents the seismic receiver offsets, which determine distances from the shot location to respective seismic receivers. The y-axis is the time. Unlike in FIG. 1, in this graph, time flows downward from the top. The continuous arched lines in this graph correspond to P-wave reflections, and the dashed arched lines correspond to S-wave reflections. Data representative of reflections from the same interface has a curved profile on this graph because the farther the seismic receivers are from the shot location, the longer paths the incident wave and reflected wave(s) travel to and from the reflecting interface. The longer paths cause delays in detecting reflections by distant seismic receivers compared to the seismic receiver close to the shot location. The deeper the reflecting interface is, the more pronounced the curvature, while reflected waves reach a larger number and more distant seismic receivers.

Data acquisition is configured to record only information related to reflected waves detected by seismic receivers within a predetermined distance (e.g., an offset range of ±6,000 m) from a shot location (which is located at "0" on the x-axis).

Waves traveling through the solid layers are also absorbed and dispersed (besides being reflected). Therefore, a predetermined incident wave can be used to explore a limited depth. As a consequence, listening time following a shot is also limited, e.g., to a few seconds. Moreover, with S-waves traveling about twice as slow through solid layers as P-waves, P-wave listening time (PLT) is shorter than S-wave listening time (SLT). During PLT, a record related to a shot includes data related to both reflected P- and S-waves. After the end of PLT until the end of SLT, the record includes only data related to reflected S-waves. PLT and SLT are defined relative to the seismic receivers within a predetermined distance from the shot location. The last reflected wave 214 in a record related to a shot is an S-wave, and it is also known as a "horizon."

Conventionally, a new shot is fired only after detecting and recording all the reflections from a previous shot. Rectangle 210 in FIG. 2 includes data related to reflections from first shot 212, and rectangle 220 includes data related to reflections from second shot 222. Rectangles 210 and 220 do not overlap.

Thus, by the time the second shot is fired, all seismic receivers within the predetermined distance left and right of the shot location have detected the last S-wave 214 reflected from the first shot. The length of rectangle 210 along the y-axis represents record time length (RTL), which may be even longer than SLT.

Productivity P is limited by the seismic record length (including dead-time when necessary), the distance between the shot locations (also called "source point interval", SPI), and the requirement for 4D accuracy (i.e., precisely reproducing the shot locations for repeated seismic surveys of the same area).

FIG. 3 is a table illustrating theoretical calculations of the maximum towing speed for various seismic record lengths and different SPIs for different previously-discussed conventional marine survey methods. The values of the towing speed have to be greater than 3.5 kts (to maintain maneuverability of the source, where 1 kts=0.514 m/s), but not greater than 8 kts (due to constraints on the towed gear). Thus, if the calculated maximum speed is lower than 3.5 kts, no value is shown in the table, and if the maximum speed is higher than 8 kts, then this (8) maximum speed value is used.

Recently, there is a tendency to increase the record length from 6-8 s to more than 10 s, due to both recording more sensors covering a larger area and to recording slower S-waves in addition to P-waves. The SPI is typically in a range of 10-50 m, but increased density is desirable. The requirement for 4D accuracy has become more stringent, with tolerances of 5-10 m for 90% of the shot points, relative to referenced (intended) positions.

These constraints make dual-vessel flip-flop methods less attractive. Accordingly, it would be desirable to provide systems and methods for marine seismic surveys with higher productivity.

SUMMARY

In order to increase productivity in a marine seismic survey, a next shot is fired before all S-wave reflections from a previous shot are detected and recorded, thereby shortening the survey duration (i.e., increasing survey's productivity).

According to one exemplary embodiment, there is a method for firing a marine seismic source towed by a vessel. The method includes firing a first shot from the marine seismic source at a first time, and firing a second shot from the marine seismic source at a second time, before the end of an S-wave listening time (SLT). During SLT, seismic receivers within a predetermined distance from the first shot's location detect S-wave reflections caused by the first shot. The method further includes recording data related to S- and P-wave reflections detected by seismic receivers.

According to another exemplary embodiment, there is a marine seismic source that includes a seismic wave generator configured to fire shots while towed and a controller. The controller is configured to trigger the seismic wave generator to fire a first shot at a first time, and then a second shot at a second time before the end of an SLT, but after the end of a PLT. During SLT, seismic receivers within a predetermined distance from the first shot's location detect S-wave reflections caused by the first shot and, during PLT, the seismic receivers detect P-wave reflections caused by the first shot.

According to another exemplary embodiment, a marine survey system includes (A) a towing vessel, (B) a marine seismic source configured to generate seismic waves by firing shots while towed by the towing vessel, (C) seismic receivers placed on the seafloor and configured to detect S- and P-wave reflections caused by the shots and emerging from under the seafloor, and (D) a controller. The controller is configured to trigger the marine seismic source to fire a first shot at a first time, and then a second shot at a second time before the end of an SLT, but after the end of the PLT. During SLT, seismic receivers within a predetermined distance from the first shot's location detect S-wave reflections caused by the first shot, and during PLT, the seismic receivers detect P-wave reflections caused by the first shot.

BRIEF DESCRIPTION OF THE DRAWINGS

The accompanying drawings, which are incorporated in and constitute a part of the specification, illustrate one or more embodiments and, together with the description, explain these embodiments. In the drawings:

FIG. 3 is a table illustrating theoretical calculations of maximum towing speed as functions of seismic record length in seconds and the source point interval (SPI) for the different conventional marine survey methods;

FIG. 11 is a table illustrating theoretical calculations of the maximum towing speed as functions of the seismic record length and SPI for different seismic survey methods according to exemplary embodiments; and FIG. 12 is a table illustrating a difference between the table in FIG. 3 and the table in FIG. 11.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of a marine survey system using ocean-bottom seismic receivers. However, the embodiments to be discussed next are not limited to these structures, but may be applied also to land seismic surveys.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Systems and methods for marine seismic surveys using a single vessel achieve higher productivity (i.e., higher towing speeds and/or shorter distances between shots) by firing a second shot before the end of SLT (S-wave listening time) related to the first shot, but after the end of PLT (P-wave listening time) related to the first shot.

Figure 1:
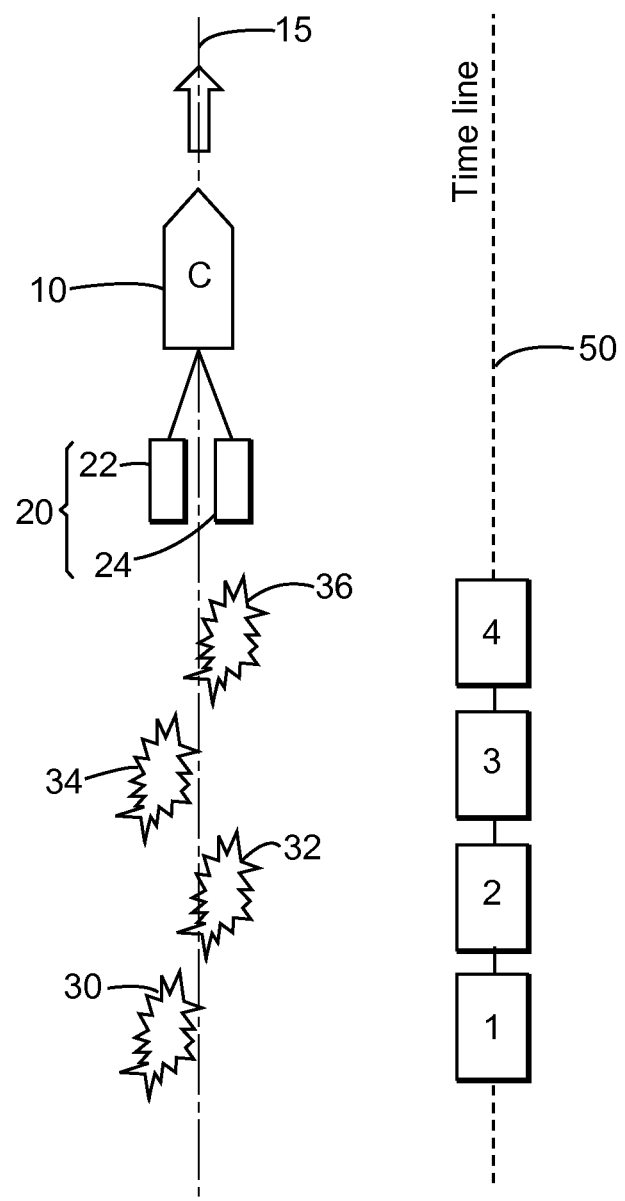
FIG. 1 is a schematic diagram of a marine survey system using a conventional method of firing the seismic source.
Figure 2:
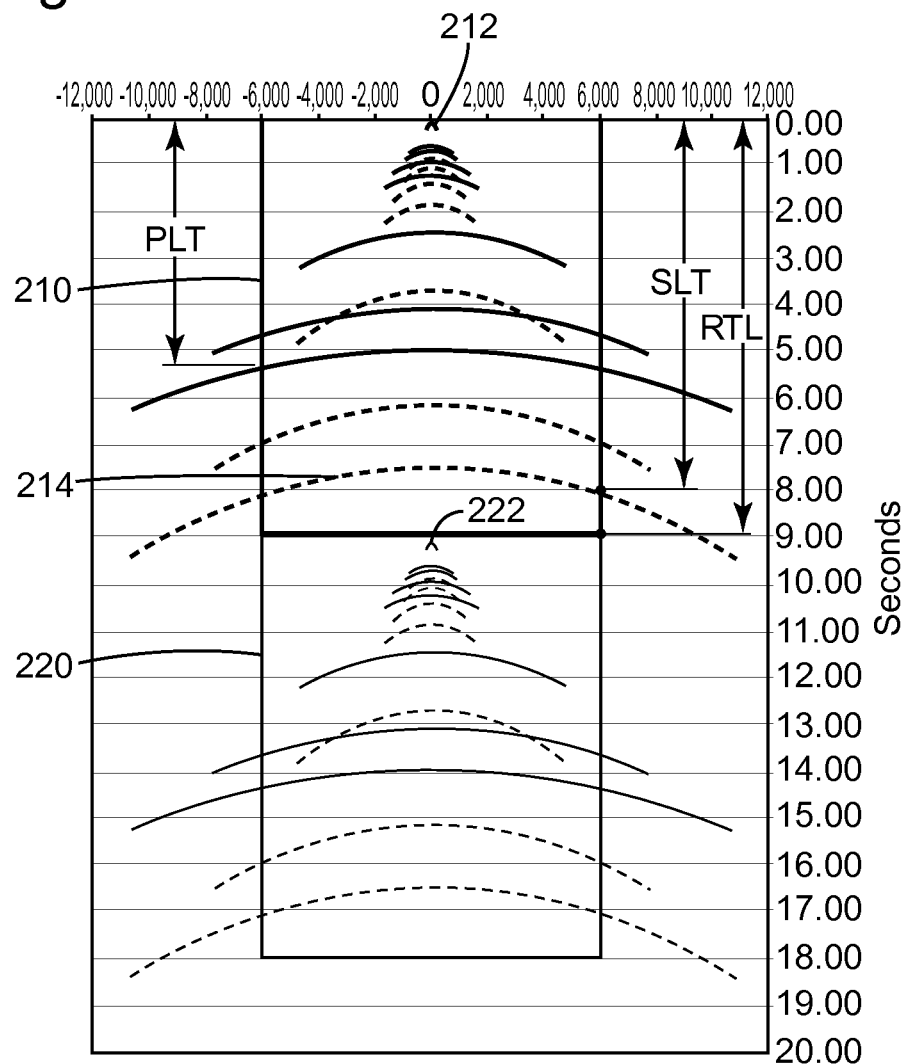
FIG. 2 is a graph illustrating data including two records following a pair of successive shots when the conventional method of firing the seismic source is used.
Figure 4:
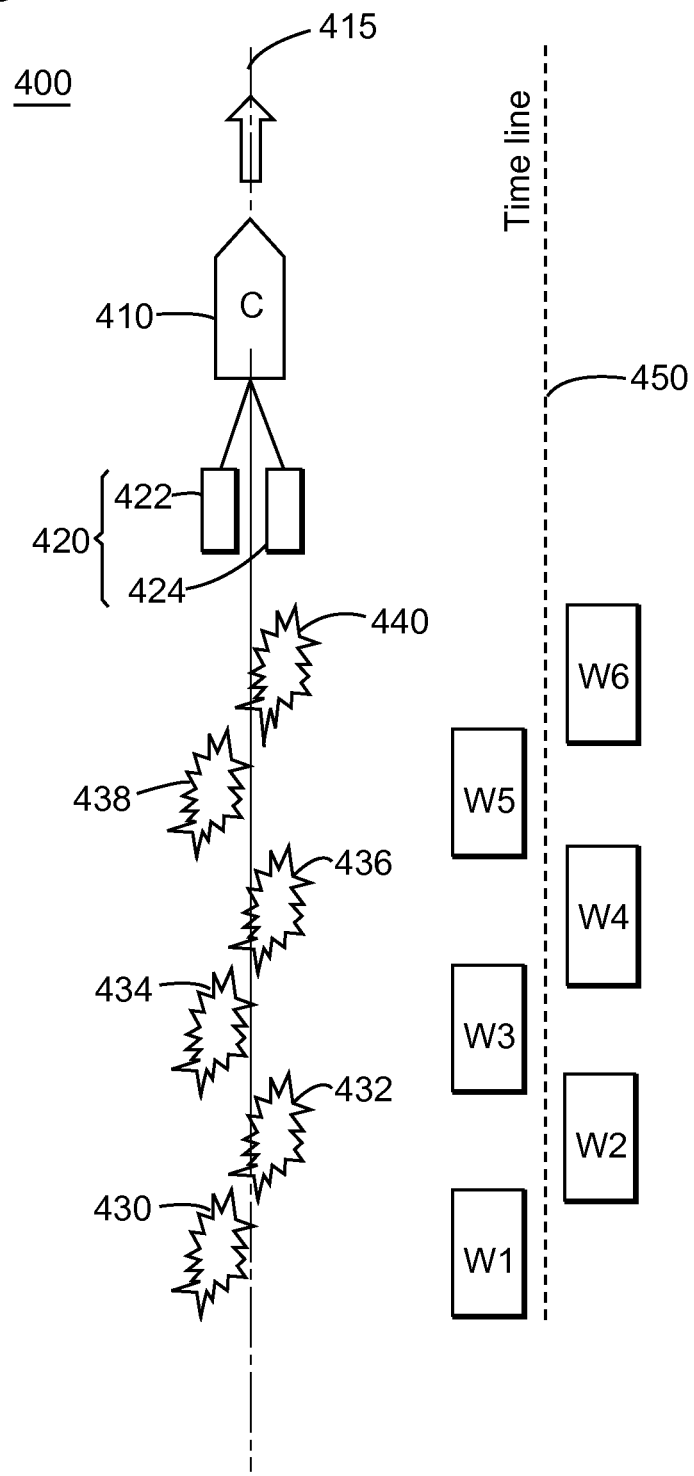
FIG. 4 is a schematic diagram of a marine survey system using a method of firing the seismic source according to an embodiment.

FIG. 4 schematically illustrates a marine survey system 400 (bird's eye view) including a vessel 410 towing a dual source 420 having sub-arrays 422 and 424, along a trajectory 415. A controller C (which may be located on vessel 410) may control sub-arrays 422 and 424. A few shot locations 430, 432, 434, 436, 438 and 440 are illustrated in FIG. 4. A corresponding time line 450 is illustrated parallel to trajectory line 415. Along time line 450, time runs from the bottom to the upper part of the line. Rectangles W1, W2, W3, W4, W5 and W6 on time line 450 represent recording times during which a data acquisition system records data related to S- and P-wave reflections detected by seismic receivers within a predetermined distance from a location of the first shot, after shots at locations 430-440, respectively. Note that rectangles W1-W6 have portions overlapping in time (i.e., when projected on time line 450) with a previous and/or a next rectangle.

In marine seismic survey system 400, a new shot is fired before all data pertaining to reflections from a previous shot have been recorded. Marine seismic survey system 400 also includes seismic receivers (OBS 4C, not shown) placed on the seafloor and configured to detected both S- and P-waves. As previously mentioned, sensors such as an OBS 4C may each include a hydrophone and a 3C geophone, or a 3D accelerometer. The marine survey system may also include a data acquisition system D (which may also be located on vessel 410) configured to collect and store data carrying information related to S- and P-wave reflections detected by seismic receivers.

Figure 5:
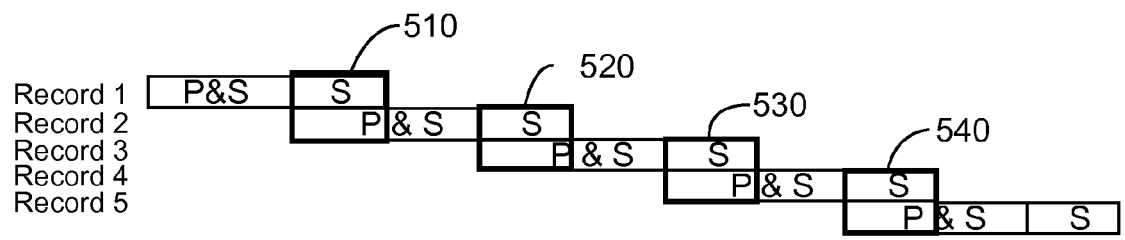
FIG. 5 is an illustration of records related to a series of shots fired using a method according to another embodiment.

In some embodiments, a shot is fired after all data related to P-wave reflections from the previous shot (as detected by seismic receivers within a predetermined distance from the shot location) have been recorded, but before all data related to S-wave reflections from the previous shot have been recorded. In other words, shots are fired after P-wave listening time (PLT) of a previous shot ends, but before S-wave listening time (SLT) of a previous shot ends, resulting in an overlap of S-wave-related data of a previous shot with P- and S-wave-related data of the later shot as illustrated in FIG. 5, where time flows from left to right and each row (record) corresponds to a shot (i.e., different rows are related to different shots). Rectangles 510, 520, 530 and 540 emphasize that S-wave-related data of one record corresponding to an earlier shot are blended with P&S-wave-related data of the next record of a later shot.

Controller C may be configured to adjust a difference between and the end of SLT and when the next shot is fired, depending on at least one of a recording duration, a target depth, and S- and P-wave velocities. Controller C may also be configured to de-blend (separate) data related to S-wave reflections from the first shot from those from the second shot.

Figure 6:
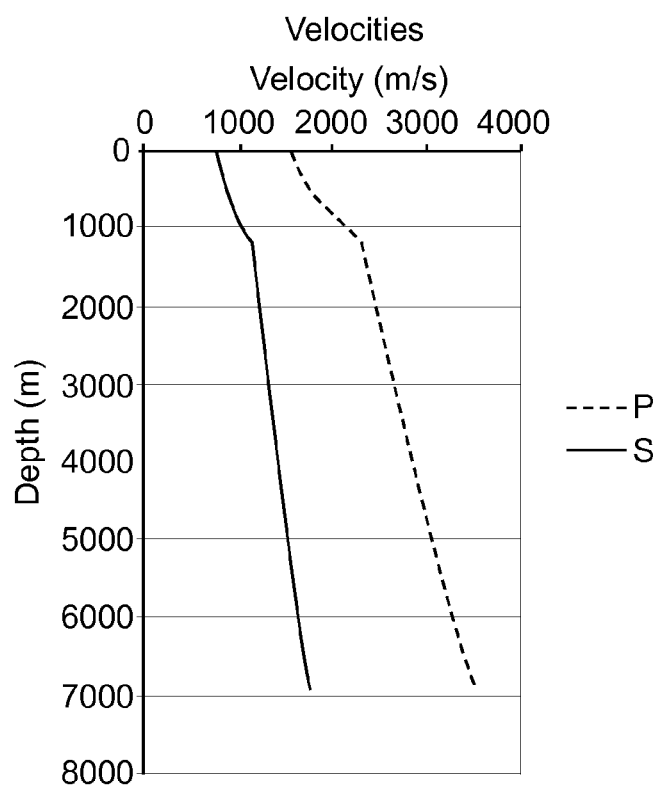
FIG. 6 is a graph illustrating S- and P-wave velocities as a function of depth.

FIG. 6 is an exemplary graph illustrating S- and P-wave velocities as a function of depth. As shown in this graph, S-wave velocity is about half of P-wave velocity. Thus, a reflected S-wave travels about twice as long as a reflected P-wave from a reflecting interface (between solid layers) to seismic detectors on the seafloor. The S-wave occurs only after the reflection and, thus, a difference between the reflected P- and S-wave times accrues only from the reflection location to the seismic receiver. Therefore, the difference between PLT and SLT (and thus, the overlapping portion of successive records) is a maximum $\frac{1}{3}$ of the record length. However, the overlap may be less than $\frac{1}{3}$ of the record length. The shot locations are geographically very close to one another, along the same towing path (even if different source arrays are fired alternately).

Figure 7:
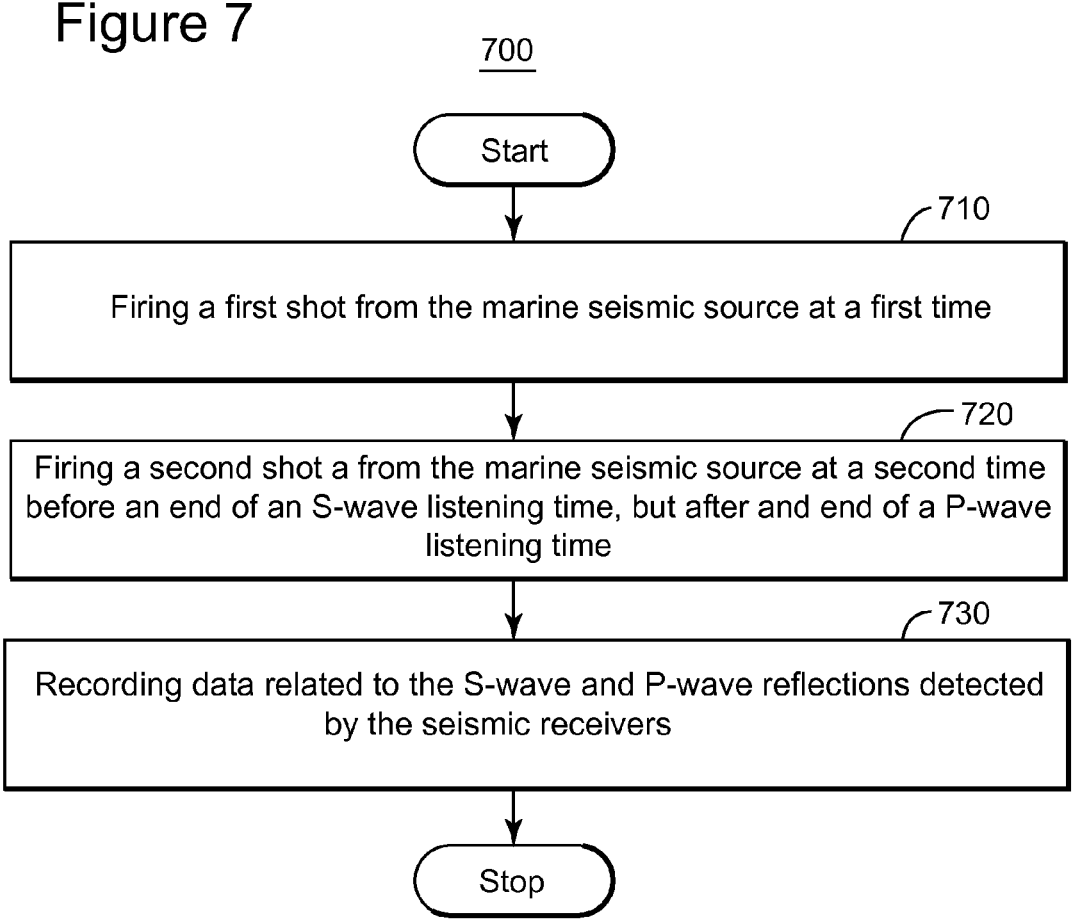
FIG. 7 is a flowchart illustrating steps performed by a method for firing a marine seismic source towed by a vessel according to another embodiment.

FIG. 7 is a flowchart illustrating steps performed by a method 700 for firing a marine seismic source towed by a vessel, according to an exemplary embodiment. Method 700 includes firing a first shot from the marine seismic source at a first time, at 710. Method 700 further includes firing a second shot from the marine seismic source at a second time, at 720. The second time is before the end of an SLT (when seismic receivers within a predetermined distance from a location of the first shot detect S-wave reflections caused by the first shot), but after the end of a PLT (when the seismic receivers detect P-wave reflections caused by the first shot).

A difference between SLT and the second time may depend on one or more of a recording duration, a target depth, and S- and P-wave velocities. For example, a difference between SLT (of about 9 s) and a second time may be about 3 s.

Method 700 also includes recording data related to S- and P-wave reflections detected by the seismic receivers, at 730. Here, data related to S-wave reflections from the first shot is blended with data related to P- and S-wave reflections from the second shot in a portion of the recorded data.

Method 700 may further include de-blending the data related to S-wave reflections from a first shot and the data related to P- and S-wave reflections from the second shot. Method 700 may also include generating one or more P-wave-based images of the underground structure (i.e., using the information related to P-wave reflections), and one or more corresponding S-wave-based images of the underground structure (i.e., using the information related to S-wave reflections). One or more merged information images of the underground structure may be created using the information related to both the P- and S-wave reflections.

Figure 8:
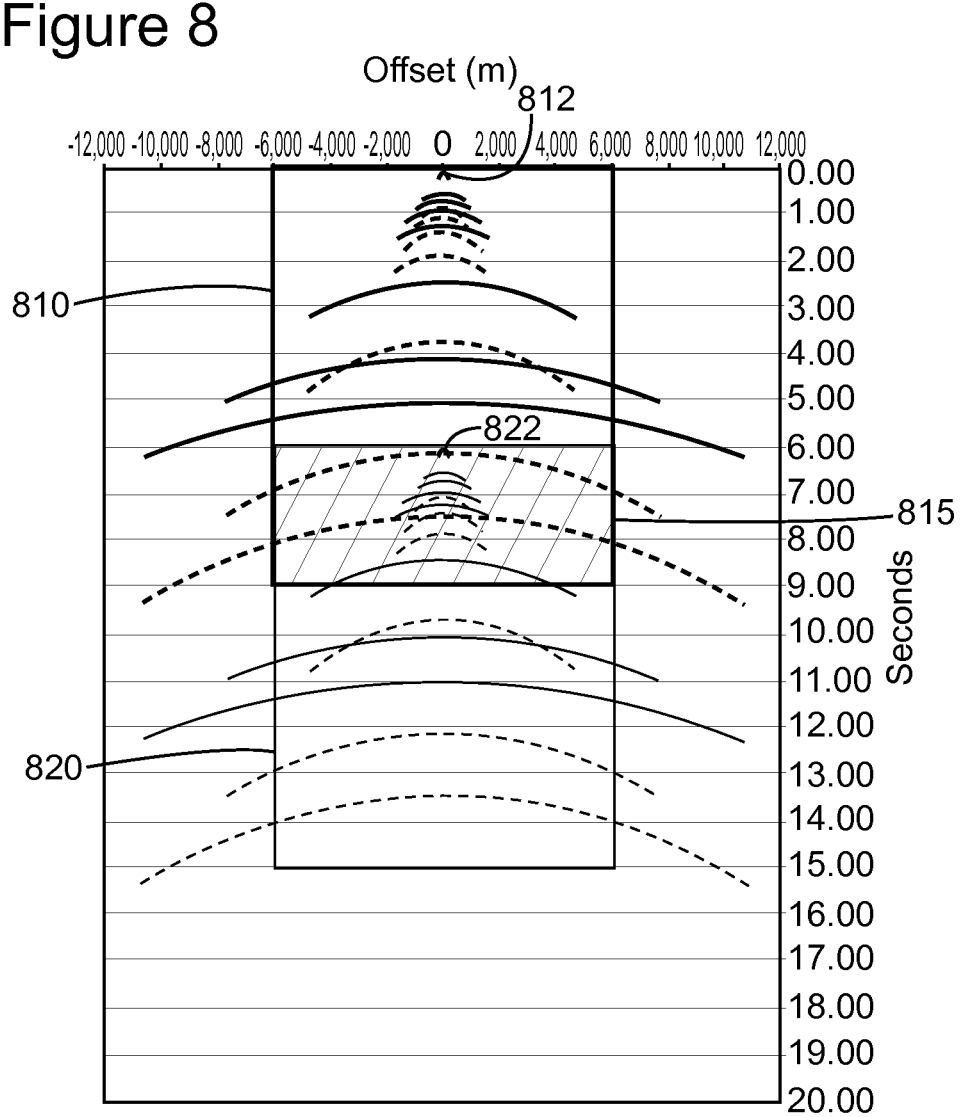
FIG. 8 is a graph illustrating data including two records following a pair of successive shots fired using a method according to an embodiment.

FIG. 8 is a graph illustrating data including two records following a pair of successive shots fired according to method 700. The x-axis of the graph represents seismic receiver offsets, which determine distances from the shot location to respective seismic receivers. The y-axis is the time. The data acquisition system is configured to collect and store only data related to reflected waves detected by seismic receivers within a predetermined distance (e.g., offset ±6,000 m) from a shot location (i.e., "0" on the x-axis).

Rectangle 810 in FIG. 8 includes data related to reflections from first shot 812, and rectangle 820 includes data related to reflections from second shot 822. Rectangles 810 and 820 overlap, having a common portion 815 that includes data related to reflected S-waves caused by first shot 812 and reflected P- and S-waves caused by second shot 822.

Figure 9:
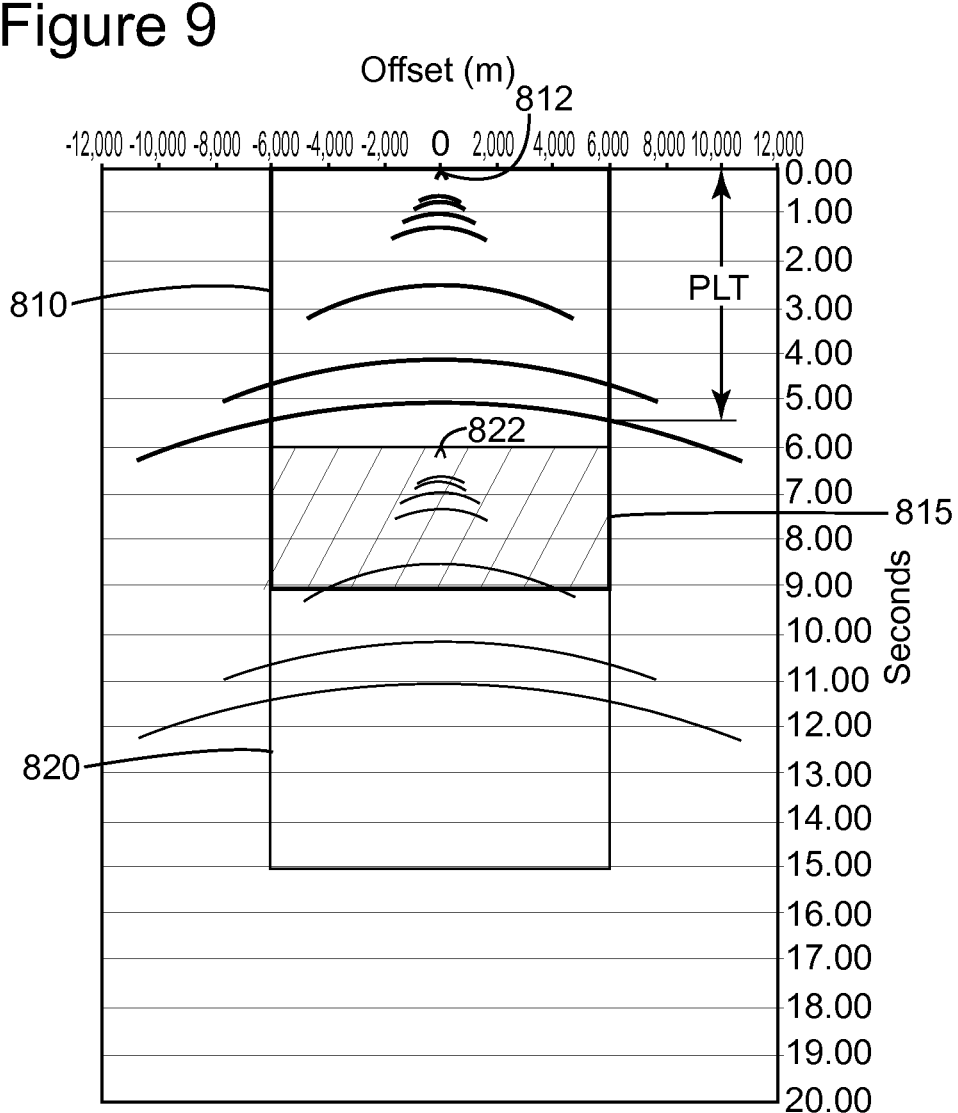
FIG. 9 is a graph illustrating P-wave-related data of two records following a pair of successive shots fired using a method according to an embodiment.

FIG. 9 corresponds to FIG. 8, but illustrates only the reflected P-waves. Since second shot 822 is fired after the end of PLT, no P-waves are located in region 815 of the graph. Thus, reflected P-waves caused by first shot 812 can easily be separated from reflected P-waves cause by second shot 822.

Figure 10:
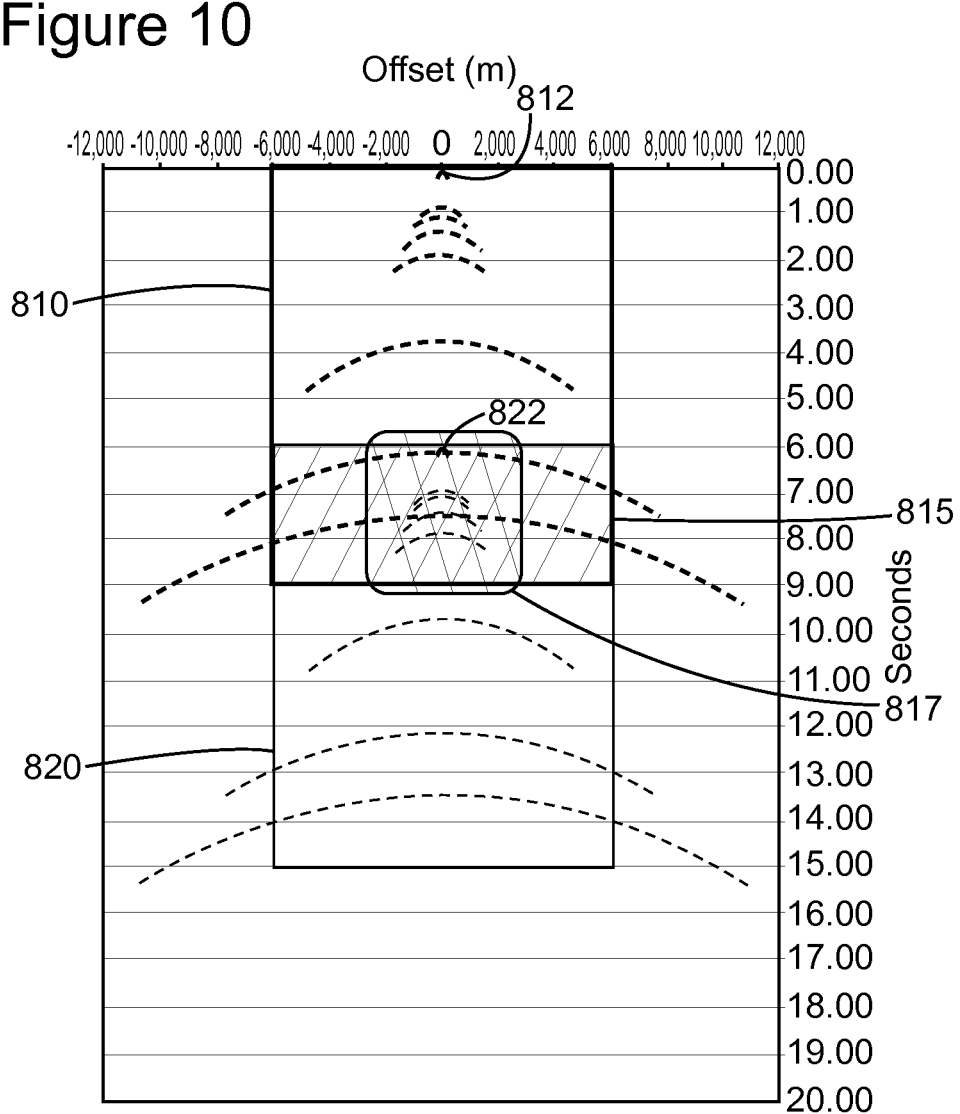
FIG. 10 is a graph illustrating S-wave-related data of two records following a pair of successive shots fired using a method according to an embodiment.

FIG. 10 corresponds to FIG. 8, but illustrates only the reflected S-waves. Since second shot 822 is fired before the end of SLT after the first shot, S-waves due to both first shot 812 and second shot 822 populate region 815. As emphasized in rectangle 817, for receivers located close to the shot locations, data related to reflected S-waves caused by first shot 812 is blended with data related to reflected S-waves caused by second shot 822.

De-blending of data related to reflected S-waves from the first shot 812 from the second shot 822 may be performed using an algorithm based on the following assumptions:
(A) consecutive/blended shots are co-located (modulo SPI);
(B) there is no blending of data related to the reflected P-waves; and
(C) only seismic receivers relatively close to the shot locations (i.e., inside rectangle 817) detect both reflected S-waves caused by first shot 812 and by second shot 822 during the record overlap.

Thus, based on (C), one approach to de-blending may be to use data related to reflected S-waves caused by a first shot as detected by the more distant seismic receivers to predict and subtract data related to reflected S-waves caused by the first shot as detected by the seismic receivers close to the shot location.

Another approach to de-blending may use the fact that both a P-wave and an S-wave emerge from each interface and, thus, for each reflected S-wave there is a corresponding reflected P-wave. Therefore, data related to reflected P-waves caused by first shot 812 may be used to predict and subtract data related to reflected S-waves caused by first shot 812.

FIG. 11 is a table illustrating theoretical calculations of the maximum towing speed as functions of the seismic record length and the source point interval (SPI) for different seismic survey methods when shots are fired according to method 700. Similar to FIG. 3, the values of the towing speed are between 3.5 and 8 kts. FIG. 12 is a table showing the enhancement (in percentages) achieved using method 700 over conventional methods of firing marine seismic sources. In this table, "OK" indicates that the maximum allowable speed of 8 kts has been attained conventionally.

The disclosed exemplary embodiments provide a marine survey system and methods for firing shots at intervals shorter than an S-wave listening time, yet larger than a P-wave listening time, for receivers within a predetermined distance from shot locations. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method for firing a marine seismic source towed by a vessel, the method comprising:
firing a first shot from the marine seismic source at a first time;
detecting, with seismic receivers, P-waves and S-wave reflections associated with the first shot;
firing a second shot from the marine seismic source at a second time, before an end of an S-wave listening time for the S-wave reflections associated with the first shot, but after an end of a P-wave listening time for the P-wave reflections associated with the first shot;
detecting with the seismic receivers, within a predetermined distance from a location of the first shot, the S-wave reflections caused by the first shot overlapped with P-wave and S-wave reflections associated with the second shot; and
recording data related to the S-wave and P-wave reflections detected by the seismic receivers.

2. The method of claim 1, wherein the seismic receivers that detect P-wave reflections caused by the first shot are located on seafloor.

3. The method of claim 1, wherein a current distance between locations of the first shot and the second shot is shorter than a previous distance between shots obtained for a previous seismic survey performed with the same seismic source's towing speed, but firing shots at a time interval longer than or equal to the S-wave listening time.

4. The method of claim 1, wherein a current towing speed is larger than a towing speed during a previous seismic survey performed with a time interval between shots longer than or equal to the S-wave listening time, so that the shots are fired in a current seismic survey at substantially similar positions as in the previous seismic survey.

5. The method of claim 1, wherein a difference between the S-wave listening time and the second time depends on at least one of a recording duration, a target depth, and S-wave and P-wave velocities.

6. The method of claim 1, the second time occurs about 3 seconds earlier than the end of the S-wave listening time of about 9 s.

7. The method of claim 1, further comprising:
de-blending information related to the S-wave reflections from the first shot and information related to S-wave reflections from the second shot in a portion of the data; and
generating a P-wave-based image of an underground structure based on information related to the P-wave reflections, a S-wave-based image of the underground structure based on information related to the S-wave reflections, and/or a merged image of underground structure based on both the information related to the P-wave reflections and the information related to the S-wave reflections.

8. The method of claim 1, wherein the marine seismic source includes two arrays of guns, the first shot being fired by a first one of the two arrays of guns and the second shot being fired by a second one of the two arrays of guns.

9. A marine seismic source, comprising:
a seismic wave generator configured to fire shots while towed; and
a controller (C) configured to trigger the seismic wave generator to fire a first shot at a first time and then a second shot at a second time, which is (1) before an end of an S-wave listening time during which seismic receivers within a predetermined distance from a location of the first shot detect S-wave reflections caused by the first shot, but (2) after an end of a P-wave listening time during which the seismic receivers detect P-wave reflections caused by the first shot, wherein the S-wave reflections caused by the first shot overlap at the seismic receivers with P-wave and S-wave reflections caused by the second shot.

10. The marine seismic source of claim 9, wherein the seismic wave generator includes two arrays of guns, the first shot being fired by a first one of the two arrays of guns and the second shot being fired by a second one of the two arrays of guns.

11. A marine seismic survey system, comprising:
a towing vessel;
a marine seismic source configured to generate seismic waves by firing shots while towed by the towing vessel;
seismic receivers placed on seafloor and configured to detect S-wave and P-wave reflections from the shots and emerging from under the seafloor; and
a controller configured to trigger the marine seismic source to fire a first shot at a first time and then a second shot at a second time, (1) before an end of an S-wave listening time during which a subset of the seismic receivers within a predetermined distance from a location of the first shot detects S-wave reflections caused by the first shot, but (2) after an end of a P-wave listening time during which the subset of the seismic receivers detects P-wave reflections caused by the first shot,
wherein the S-wave reflections caused by the first shot overlap with P-wave and S-wave reflections caused by the second shot.

12. The marine seismic survey system of claim 11, further comprising:
a data acquisition system configured to gather as data, information related to the S-wave and P-wave reflections detected by the seismic receivers,
wherein, in a portion of the data, information related to the S-wave reflections caused by the first shot is blended with information related to S-wave and P-wave reflections caused by the second shot.

13. The marine seismic survey system of claim 12, wherein, in the data, the information related to the P-wave reflections caused by the first shot is not blended with information related to P-wave reflections caused by the second shot.

14. The marine seismic survey system of claim 11, wherein a current distance between locations of the first shot and the second shot is shorter than a previous distance between shots obtained for a previous seismic survey performed with the same seismic source's towing speed, but firing shots at a time interval longer than or equal to the S-wave listening time.

15. The marine seismic survey system of claim 11, wherein a current towing speed is larger than a towing speed during a previous seismic survey performed with a time interval between shots longer than or equal to the S-wave listening time, so that the shots to be fired in a current seismic survey at substantially similar positions as in the previous seismic survey.

16. The marine seismic survey system of claim 11, wherein the controller is configured to adjust a difference between the S-wave listening time and the second time depending on at least one of a recording duration, a target depth, and S-wave and P-wave velocities.

17. The marine seismic survey system of claim 11, wherein the controller is configured to trigger the second shot at the second time about 3 seconds earlier than the end of the S-wave listening time of about 9 s.

18. The marine seismic survey system of claim 12, further comprising:
a data processing unit configured to de-blend, for the portion of the data, the information related to the S-wave reflections caused by the first shot and the information related to S-wave and P-wave reflections caused by the second shot, and to generate one or more of a P-wave-based image of an underground structure based on information related to the P-wave reflections, an S-wave-based image of the underground structure based on information related to the S-wave reflections, and/or a merged image of underground structure based on both the information related to the P-wave reflections and the information related to the S-wave reflections.

19. The marine seismic survey system of claim 11, wherein the marine seismic source includes two arrays of guns and the controller triggers a first of the two arrays of guns to fire the first shot and a second of the two arrays of guns to fire the second shot.

20. The marine seismic survey system of claim 11, wherein the seismic receivers are ocean bottom sensors configures to detect both P-waves and S-waves.

* * * * *